April 18, 1939. V. S. HILLOCK Plant Pat. 326
ROSE
Filed May 27, 1937
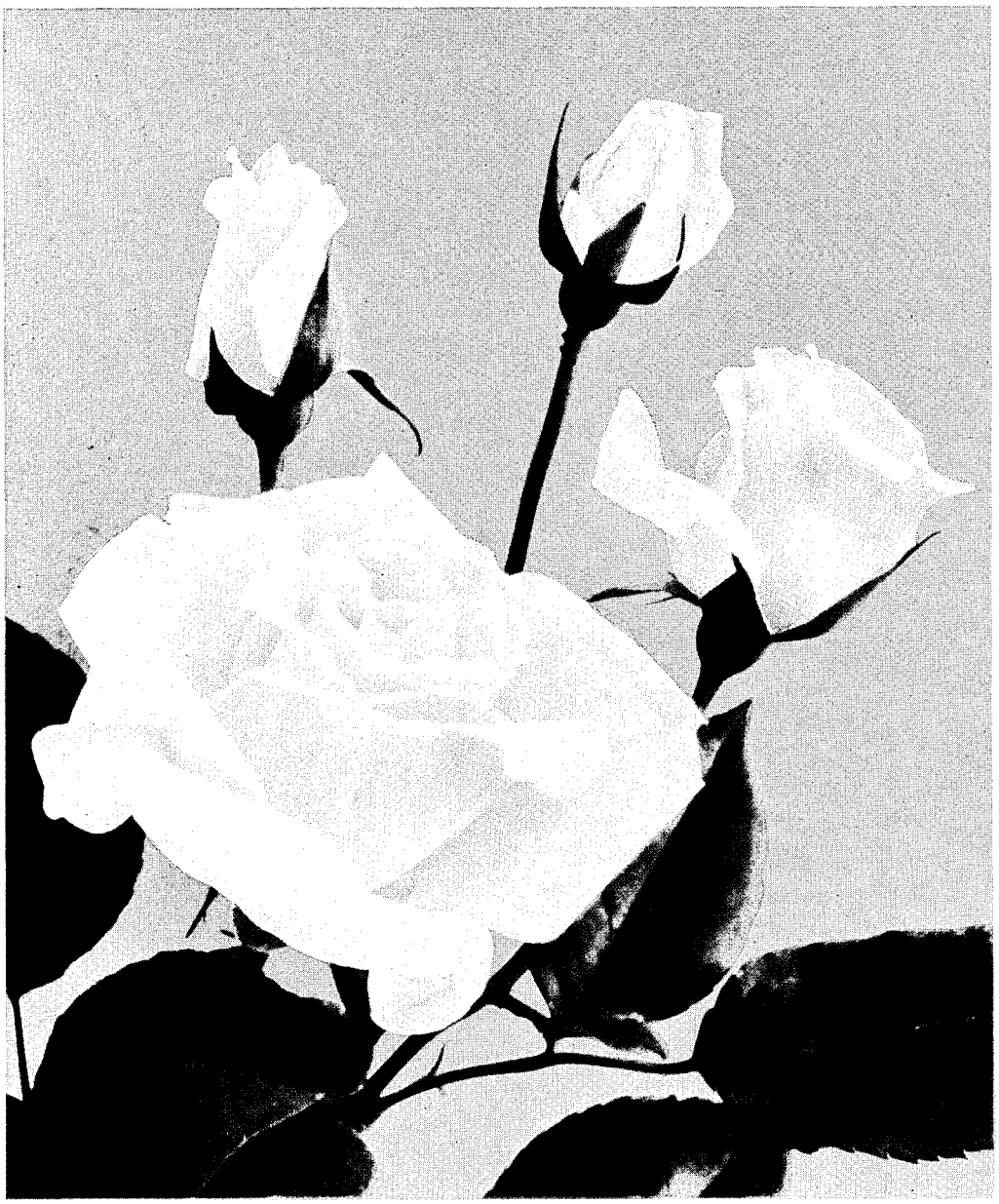
INVENTOR
Verne Stone Hillock
By Orville M. Kile
Plant Patent Agent Patented Apr. 18, 1939

Plant Pat. 326

UNITED STATES PATENT OFFICE

326

ROSE

Verne Stone Hillock, Arlington, Tex.

Application May 27, 1937, Serial No. 145,130

1 Claim. (Cl. 47—61)

This new variety is of the Hybrid Tea class and resulted from the growing of a seedling from an undisseminated climbing sport of the rose Mrs. Pierre S. du Pont, the seed itself arising from self-fertilization or accidental cross pollination. I discovered the climbing sport of Mrs. Pierre S. du Pont several years ago and this was used as a seed bearer. Budded plants from seedlings of this climbing sport were nurtured and selected until in the fourth year only one was retained. I have reproduced this new variety in considerable numbers through five bud generations and have thoroughly established its permanence and novelty.

The purpose of this invention was to improve the variety Mrs. Pierre S. du Pont in important particulars.

The accompanying illustration shows in full color and approximately full size, in the original, three buds in opening stages and a blossom in its prime. The following description is based on observations made at Arlington, Texas, over a period of years. Except where otherwise noted, observations relate to buds and blossoms of the first burst in springtime. Color references are to Ridgeway's Color Standards and Nomenclature wherever plate numbers are indicated.

*The plant*

Growth:

Vigorous and compact.

Form:

Bush.

Foliage:

*Leaflets.*—Usually five, occasionally seven.

*Size.*—Medium to large.

*Quantity.*—Abundant (more abundant than the average hybrid tea in the approximate ratio of five to three).

*Color.*—New foliage: upper side, Leaf Green (Plate XLI); under side, slate green. Old foliage: upper side, dark green; lower side, Leaf Green (Plate XLI).

*Shape.*—Oval pointed.

*Texture.*—Upper side, somewhat glossy (waxy), though not markedly so. As the foliage ages it assumes a somewhat leathery appearance. Under side, smooth. Ribs and veins numerous.

*Edge.*—Serrated with single serrations.

*Leaf stem.*—Green on both new and old foliage. Habitually carries prickles in moderate number.

*Stipules.*—Medium length. Broad when the foliage is large, otherwise below average in width.

Wood:

*New wood.*—Color green, quickly becoming purple-bronze, the change often beginning even before the blossom is shed.

*Old wood.*—Deep purple-bronze with many longitudinal stripings. Bark smooth.

Thorns:

*Quantity.*—On main stalks from base, few. On laterals from stalks, few.

*Form.*—Hooked very slightly. Rather small. Narrow base.

*Color when young.*—Pink to red.

*Color when old.*—Brown.

*Position.*—Markedly irregular.

*Prickles.*—None.

*Short needles.*—None.

Disease resistance:

Markedly resistant to mildew and black spot.

Stems:

Medium to long. Of medium strength to strong.

*The bloom*

Blooming Habit:

This rose tends to bloom in monthly bursts as is the habit of hybrid teas. But the bursts tend to overlap because of long duration and established bushes are seldom out of bloom during the summer except during August.

The Bud:

*Size.*—Medium.

*Form.*—Pointed. "Flutes" when opening.

*Weather effects.*—Not affected by wet weather. Never "balls". Not affected by heat except that it will burn in extreme heat as any rose will do. Particularly resistant to cold.

*Color.*—During the first burst of springtime the reverse of the petal is of a color which lies between Capucine Yellow (Plate III) and Mikado Orange (Plate III) with a small Lemon Chrome (Plate IV) base at the point of attachment. The inside of the petal is slightly lighter than the reverse side (near Deep Chrome on Pl. III) and carries a uniform color throughout. The autumn color is the same as that of spring, but the summer color is slightly lighter and is more nearly Light Orange Yellow (Plate III).

*Sepals.*—The sepals are not serrated. Some are branched, others not. Occasionally a sepal is hooded. Sepals extend above the bud when the bud is small but turn back as the bud unfurls.

*Calyx.*—Conical and smooth.

*Peduncle.*—Moderately long. Smooth. Although of moderate sturdiness it is adequate to support the blossom.

*Opening.*—Bud opens well in all weathers.

The Blossom:

*Size.*—Medium to large. Three and one-half to five inches in diameter.

*Borne.*—Singly and in sprays.

*Form.*—Cupped.

*Petalage.*—Averages thirty-five petals. Under adverse conditions the petalage is somewhat reduced but with petaloids added. In late autumn the petalage is sometimes increased to fifty.

*Color.*—(See bud.) The color is the same as the color of the bud except that the tip of the petal sometimes fades slightly as the blossom opens.

*Petals.*—Texture—average thickness. Soft to the touch. Appearance—smooth on both surfaces. Often markedly veined during spring and fall. Veining less apparent during hot weather. Form—outer petals are almost round when pressed flat. Inner petals oval. Scalloped. Arrangement—imbricated. Persistence—drop off cleanly. Fragrance—strong. Same as Mrs. Pierre S. du Pont rose.

*Lasting quality.*—The blossom is long lasting either as a cut flower or on the bush.

*Genital organs*

Stamens:

*Anthers.*—Larger than average hybrid tea. Color brown and yellow. Many.

*Filaments.*—Medium to long, uneven in length. Color mostly pink, some yellow. Arrangement regular around styles.

Pistils:

*Styles.*—Bunched. Uneven length. Short to medium. Medium number. Pink, shading to whitish-yellow at base.

*Stigmas.*—Yellow.

*Ovaries.*—Usually all tightly enclosed. Occasionaly a few protrude.

*Fruit.*—The variety is fertile with its own pollen. Form—flat-headed. Aspect—smooth. Color at maturity—Brownish-yellow. Sepals—permanent. Recurved.

*Comparison*

The labors of origination were undertaken with the direct intent or hope of improving the variety Mrs. Pierre S. du Pont. This new variety more nearly resembles Mrs. Pierre S. du Pont than any other rose in commerce but differs from it in several important points. The wood of both varieties is much alike both in color and in texture, both being hard-wooded varieties. Foliage of the two varieties differs somewhat, the foliage of this variety being larger and darker green, never showing the blue-green sheen frequently displayed by the Mrs. Pierre S. du Pont.

The color of the bloom of this variety is distinctly richer and deeper, differing from the color of Mrs. Pierre S. du Pont in the direction of orange. The color is held much better by this new variety.

The bud of this variety is longer and is pointed, while the short bud of the Mrs. Pierre S. du Pont is ovoid. The bud of this variety flutes while opening while the bud of the Mrs. Pierre S. du Pont does not, the latter rose being practically without an intermediate stage in opening.

The petalage of this variety is much greater than that of the Mrs. Pierre S. du Pont—which was one of the more important objectives. This difference is most marked in the sprays. Both varieties bloom singly and in sprays. The sprays of the Mrs. Pierre S. du Pont habitually show a center blossom of appreciable worth; but the spur blossoms on those sprays, blooming later and concurrently, though of value in the bud stage quickly become of little or no worth upon opening because of want of petalage and because of flimsy petal texture. On the other hand, in the present variety all blossoms of the sprays are of excellent quality because of greater petalage.

The petal texture of this variety is patently superior to the petal texture of the Mrs. Pierre S. du Pont. The spur blossoms of this variety, because of added petalage and superior petal texture, are far superior to the spur blossoms on the sprays of the Mrs. Pierre S. du Pont. They are, in fact, habitually superior to the center blossoms of the Mrs. Pierre S. du Pont sprays.

The gains in color, petalage, and petal texture are not offset by decreased productiveness. Both varieties are very highly productive. Unpruned bushes of this variety standing in the field at Arlington produced from fifty to seventy-five blossoms per plant during the first burst of the past spring.

Having thus disclosed my invention, I claim:

A variety of rose substantially as shown and described, characterized particularly by its resistance to disease and cold, its superior bud, its abundant dark green foliage, and its blossoms of distinctive color and numerous petals of improved texture as compared with its nearest known competitor, the Mrs. Pierre S. du Pont rose.

VERNE STONE HILLOCK.